US008684941B2

(12) United States Patent
Nishioka et al.

(10) Patent No.: US 8,684,941 B2
(45) Date of Patent: Apr. 1, 2014

(54) ELECTRONIC SPHYGMOMANOMETER (75) Inventors: Takanori Nishioka, Kyoto (JP); Yoshihiko Sano, Kyoto (JP); Atsushi Kawano, Takarazuka (JP); Mika Eto, Takatsuki (JP); Kenji Aridome, Takatsuki (JP); Kotaro Suzuki, Shanghai (CN); Masahiko Yumoto, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 140 days.

(21) Appl. No.: 13/155,829

(22) Filed: Jun. 8, 2011

(65) Prior Publication Data
US 2011/0237963 A1 Sep. 29, 2011

Related U.S. Application Data (63) Continuation of application No. PCT/JP2009/070092, filed on Nov. 30, 2009.

(30) Foreign Application Priority Data

Dec. 8, 2008 (JP) ................. 2008-312157

(51) Int. Cl.
*A61B 5/02* (2006.01)
(52) U.S. Cl.
USPC ............ 600/493; 600/495; 600/496; 600/503
(58) Field of Classification Search
USPC ................................. 600/480–495
See application file for complete search history.

(56) References Cited

U.S. PATENT DOCUMENTS

| 6,511,435 | B1 | 1/2003 | Bluth et al. |
| 6,893,402 | B2 * | 5/2005 | Freund et al. ................. 600/485 |
| 2004/0077958 | A1 | 4/2004 | Kato et al. |

FOREIGN PATENT DOCUMENTS

| JP | 2002-034937 A | 2/2002 |
| RU | 2299008 C2 | 5/2007 |
| WO | 02/39893 A1 | 5/2002 |

OTHER PUBLICATIONS

Patent Abstracts of Japan, Publication No. 2002-034937, Publication Date: Feb. 5, 2002, 1 page.
International Search Report issued in PCT/JP2009/070092 mailed on Jan. 19, 2010, and English translation thereof, 2 pages.
Office Action issued in corresponding Russian Application No. 2011128005/14(041547) dated Oct. 23, 2013, and English translation thereof (8 pages).

* cited by examiner

*Primary Examiner* — Michael Kahelin
*Assistant Examiner* — Mitchell Alter
(74) *Attorney, Agent, or Firm* — Osha Liang LLP (57) ABSTRACT An electronic sphygmomanometer determines whether a position of a measurement site falls within a proper range, and notifies whether the position of the measurement site falls within the proper range. When determination is made that a time in which the position of the measurement site falls within the proper range is not less than a predetermined time (for example, 2 seconds), measurement of a blood pressure is automatically started. When determination is made that a time in which the position of the measurement site is out of the proper range is not less than a predetermined time (for example, 5 seconds), the measurement of the blood pressure is started. Further, whether the position of the measurement site falls within the proper range is notified while correlated with the measurement result.

7 Claims, 9 Drawing Sheets

ELECTRONIC SPHYGMOMANOMETER

TECHNICAL FIELD

The present invention relates to an electronic sphygmomanometer, particularly to a wrist type electronic sphygmomanometer that can determine whether a position of a blood pressure measurement site falls within a proper range.

BACKGROUND ART

Generally, in a sphygmomanometer, a blood pressure value can correctly be obtained by performing measurement in a state in which a position of a blood pressure measurement site is aligned with a height of a heart. This is because, due to a weight of the blood pressure, the blood pressure value is increased when the measurement site is measured at a position lower than the heart and the blood pressure value is decreased when the measurement site is measured at a position higher than the heart.

Therefore, as illustrated in International Publication WO 2002/039893 (Patent Document 1), there is a wrist type sphygmomanometer that includes angle detection means (angle sensor) to determine whether a measurement posture is proper and notifies whether the measurement posture is proper. In the conventional sphygmomanometer, the measurement is started only when a pressure reference position of the sphygmomanometer falls within the proper range in which the height of the pressure reference position is substantially identical to that of the heart. In this sphygmomanometer, for example, a two-axis angle detection sensor is provided to detect angles in a pitch direction and a roll direction of a front arm, and a difference in height between the position of the measurement site and the position of the heart is calculated based on the detection values of the angles in the two directions.

Patent Document 1: International Publication WO 2002/039893

SUMMARY OF INVENTION

In the conventional technique as described above, measurement is started only when the position of the measurement site falls within the proper range. Accordingly, for a user (person to be measured) who can hardly set the position of the measurement site into the proper range due to a physical feature (for example, a user who has difficulty in raising a wrist), the measurement cannot be performed hour by hour.

There is also a user who does not read an instruction manual because the user has no (little) use experience of the sphygmomanometer immediately after purchase. Such users may not notice that the position of the measurement site needs to fall within the proper range in order to start the measurement. Therefore, the user may feel uncomfortable because of the measurement not being started for a long time even though the user wants to start the measurement.

Therefore, one or more embodiments of the present invention provides an electronic sphygmomanometer that can improve usability while including the angle sensor to guide the position of the measurement site into the proper range.

According to one or more embodiments of the invention, an electronic sphygmomanometer includes: a cuff that is worn around a predetermined measurement site; a pressure sensor that detects a cuff pressure signal indicating a pressure in the cuff; an angle sensor that detects an angle of the cuff with respect to a predetermined reference direction; a position determining unit that determines whether a position of the measurement site falls within a proper range based on an output from the angle sensor; a notification unit that notifies whether the position of the measurement site falls within the proper range; a time determining unit that determines whether a first time indicating a time in which the position of the measurement site falls within the proper range is not less than a first reference time; and a measurement control unit that controls measurement of a blood pressure based on the cuff pressure signal by taking the determination that the first time is not less than the first reference time as a first opportunity. The time determining unit further determines whether a second time indicating a time in which the position of the measurement site is out of the proper range is not less than a second reference time longer than the first reference time. The measurement control unit starts the measurement by taking the determination that the second time is not less than the second reference time as a second opportunity. The notification unit further notifies whether the position of the measurement site falls within the proper range while the position of the measurement site is correlated with a measurement result when the measurement control unit outputs the measurement result.

According to one or more embodiments of the present invention, the time determining unit initializes a currently-measured time when a determination result of the position determining unit is changed.

According to one or more embodiments of the present invention, the electronic sphygmomanometer further includes a storage unit in which position identification data indicating whether the position of the measurement site falls within the proper range is stored while correlated with the measurement result.

According to one or more embodiments of the present invention, the measurement result and the position identification data are stored in the storage unit while correlated with personal identification data identifying a person to be measured.

According to one or more embodiments of the present invention, the time determining unit further determines whether an elapsed time since a user issues an instruction to start the measurement is not less than a third time which is longer than the second reference time, and the measurement control unit starts the measurement by taking the determination that the elapsed time is not less than the third reference time as a third opportunity.

According to one or more embodiments of the present invention, the notification unit includes a light emitting unit that emits first color light and second color light, and a notification processing unit that, in order to notify whether the position of the measurement site falls within the proper range, causes the light emitting unit to emit the first color light when the position of the measurement site falls within the proper range, and causes the light emitting unit to emit the second color light when the position of the measurement site is out of the proper range.

According to one or more embodiments of the present invention, the notification unit includes a display unit that displays the measurement result, and a notification processing unit that displays information indicating whether the position of the measurement site falls within the proper range on the display unit in order to notify whether the position of the measurement site falls within the proper range.

According to one or more embodiments of the present invention, similar to the conventional technique, the person to be measured is notified whether the position of the measurement site falls within the proper range, and the measurement is automatically started when the position of the measurement site is maintained within the proper range.

Further, according to one or more embodiments of the present invention, the measurement can be automatically started even if the position of the measurement site is maintained out of the proper range. Therefore, the usability can be improved.

According to one or more embodiments of the present invention, when the measurement control unit outputs the measurement result, whether the position of the measurement site falls within the proper range is further notified while the position of the measurement site is correlated with the measurement result. Accordingly, the person to be measured can easily determine whether the currently-output measurement result is obtained in the proper measurement posture.

DETAILED DESCRIPTION OF INVENTION

Embodiments of the present invention will be described in detail with reference to the drawings. The same reference numerals are denoted to the same or corresponding portions in the figures, and the description thereof will not be repeated.
<Regarding Appearance and Configuration>

First, an appearance and a configuration of an electronic sphygmomanometer according to an embodiment of the present invention (hereinafter referred to as a "sphygmomanometer") will be described.
(Regarding Appearance)

Figure 1:
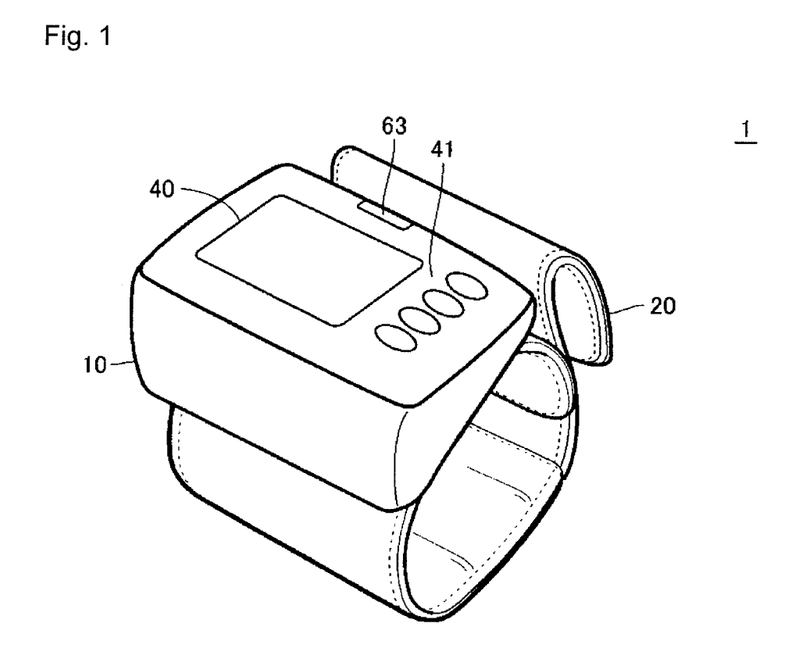
FIG. 1 is a perspective view of an appearance of a sphygmomanometer according to an embodiment of the present invention.

FIG. 1 is a perspective view of an appearance of a sphygmomanometer 1 according to an embodiment of the present invention.

Referring to FIG. 1, the sphygmomanometer 1 includes a main body 10 and a cuff 20 that can be worn around a wrist of a person to be measured. The main body portion 10 is attached to the cuff 20. A display unit 40 including an LCD (Liquid Crystal Display), for example, and an operation unit 41 that receives an instruction from a user (typically, person to be measured) are arranged on a surface of the main body 10. For example, the operation unit 41 includes a plurality of switches.

(Regarding Hardware Configuration)

Figure 2:
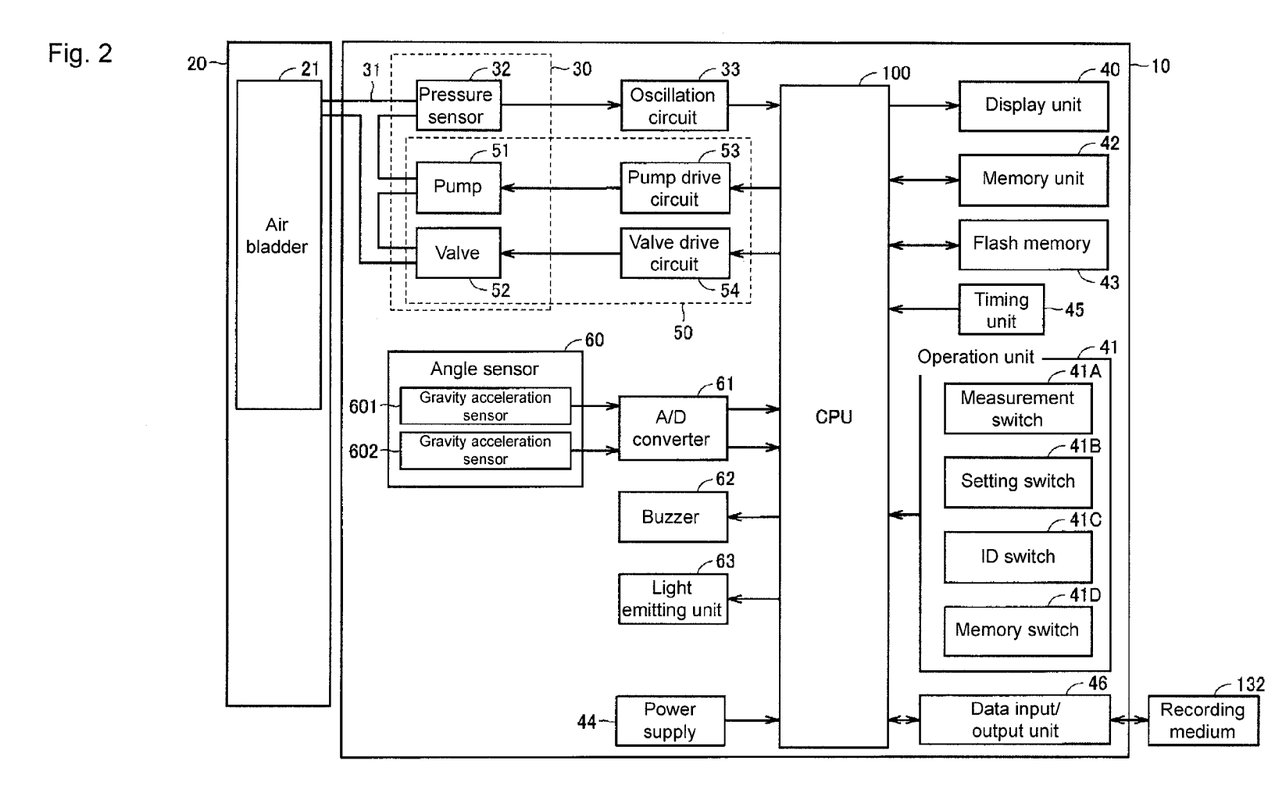
FIG. 2 is a block diagram illustrating a hardware configuration of the sphygmomanometer according to an embodiment of the present invention.

FIG. 2 is a block diagram illustrating a hardware configuration of the sphygmomanometer 1 according to an embodiment of the present invention.

Referring to FIG. 2, the cuff 20 of the sphygmomanometer 1 includes an air bladder 21. The air bladder 21 is connected to an air system 30 through an air tube 31.

In addition to the display unit 40 and the operation unit 41, the main body 10 includes the air system 30, a CPU (Central Processing Unit) 100 that intensively controls each unit to perform various pieces of calculation processing, a memory unit 42 in which various programs and various pieces of data are stored, a nonvolatile memory (for example, a flash memory) 43 in which a measured blood pressure is stored, a power supply 44 that supplies electric power to the CPU 100 and the like, a timing unit 45 that performs a timing operation, a data input/output unit 46 that receives an input of data from the outside, an angle sensor 60 that detects an angle of the cuff 20 with respect to a predetermined reference direction, an ND (analog-to-digital) converter 61 that converts an analog signal from the angle sensor 60 into a digital signal, a buzzer 62 that issues an alert sound and the like, and a light emitting unit 63 that emits at least two colors of light.

The operation unit 41 includes a measurement switch 41A that receives an instruction to start and stop the measurement, a setting switch 41B that receives an instruction to set and change various functions, an ID switch 41C that is operated to input ID (Identification) information for identifying a person to be measured, and a memory switch 41D that receives an instruction to read measurement recording data such as a blood pressure value.

The air system 30 includes a pressure sensor 32 that detects a pressure (cuff pressure) in the air bladder 21, a pump 51 that supplies air to the air bladder 21 to increase the cuff pressure, and a valve 52 that is opened and closed to discharge or enclose the air of the air bladder 21.

The main body 10 also includes an oscillation circuit 33, a pump drive circuit 53, and a valve drive circuit 54 in association with the air system 30.

The pressure sensor 32 is a capacitance type pressure sensor in which a capacitance value is changed by the cuff pressure. The pressure sensor 32 is not limited to the capacitance type, but may be a piezoresistance type. The oscillation circuit 33 outputs a signal having an oscillating frequency corresponding to the capacitance value of the pressure sensor 32 to the CPU 100. The CPU 100 detects a pressure by converting the signal obtained from the oscillation circuit 33 into the pressure. The pump drive circuit 53 controls drive of the pump 51 based on a control signal provided from the CPU 100. The valve drive circuit 54 controls opening and closing of the valve 52 based on a control signal given from the CPU 100.

The pump 51, the valve 52, the pump drive circuit 53, and the valve drive circuit 54 constitute an adjustment mechanism 50 that adjusts the cuff pressure. It should be recognized that the device for adjusting the cuff pressure is not limited thereto.

For example, the data input/output unit 46 reads and writes a program or data from and in a removable recording medium 132. Alternatively, the data input/output unit 46 may transmit and receive the program or data to and from an external computer (not illustrated) through a communication line.

The angle sensor 60 detects the angle of the cuff 20 attached to a measurement site in order to detect an angle of an axis of the measurement site (wrist) with respect to the predetermined reference direction. In the sphygmomanometer 1 according to one or more embodiments of the present invention, the angle sensor 60 is disposed at a predetermined position in the main body 10 because the main body 10 is bonded onto an outer surface of the cuff 20. However, embodiments of the present invention are not limited thereto, and the angle sensor 60 may be disposed at a predetermined position of the cuff 20.

For example, the angle sensor 60 is a two-axis angle sensor, and the angle sensor 60 includes a gravity acceleration sensor 601 in a pitch direction of a front arm and a gravity acceleration sensor 602 in a roll direction of the front arm. In this case, for example, the "reference direction" that becomes a reference of angular detection is set to a vertical direction.

The A/D converter 61 inputs signals from the two gravity acceleration sensors 601 and 602, and converts the signals into digital signals. The A/D converter 61 separately provides the converted digital signals to the CPU 100. Therefore, the CPU 100 can calculate a deviation width (typically, a difference in height) between the wrist that is the measurement site and a virtual heart position.

The angle sensor 60 is not limited to the two-axis angle sensor, but may be a uniaxial or three-axis angle sensor. Alternatively, as described in Patent Document 1, the angle sensor may be provided not only in the main body 10 but also to an upper arm.

For example, the light emitting unit 63 includes two LEDs (Light Emitting Diodes) that separately emit blue light and red light. The light emitting unit 63 may include one LED or another type of light source (such as a filament bulb and a discharge lamp) as long as the light emitting unit 63 can emit at least two colors of light. The colors of emitted light are not limited to the blue and red as long as the colors are contrastive colors.

In the sphygmomanometer 1 according to one or more embodiments of the present invention, as illustrated in FIG. 1, the main body 10 is attached to the cuff 20. Alternatively, similar to an upper arm type sphygmomanometer, the separated main body 10 and cuff 20 may be connected by an air tube (the air tube 31 in FIG. 2). In such cases, the angle sensor 60 may be disposed in a predetermined position of not the main body 10 but the cuff 20.

Although the cuff 20 includes the air bladder 21, a fluid supplied to the cuff 20 is not limited to air, but may be a liquid or gel. Alternatively, embodiments of the present invention are not limited to the fluid, but may be uniform and fine particles such as microbeads.

According to one or more embodiments of the present invention, the predetermined measurement site is the wrist, but is not necessarily limited thereto.

(Regarding Functional Configuration)

Figure 3:
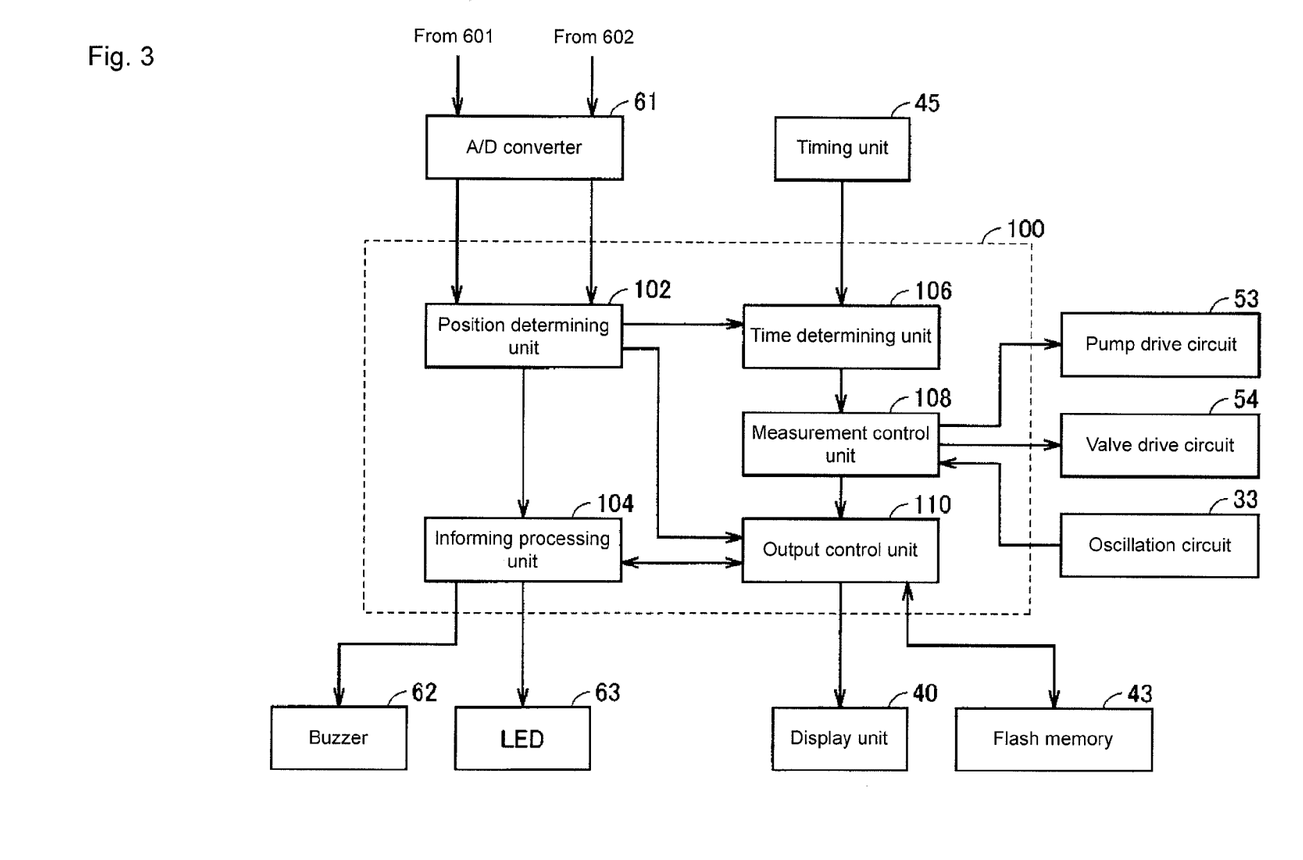
FIG. 3 is a functional block diagram illustrating a functional configuration of the sphygmomanometer according to an embodiment of the present invention.

FIG. 3 is a functional block diagram illustrating a functional configuration of the sphygmomanometer 1 according to an embodiment of the present invention.

Referring to FIG. 3, the CPU 100 includes a position determining unit 102, a notification processing unit 104, a time determining unit 106, a measurement control unit 108, and an output control unit 110 as functions thereof. For the sake of simplifying the description, FIG. 3 only illustrates peripheral hardware that directly transmits and receives a signal to and from each functional unit of the CPU 100.

The position determining unit 102 determines whether the position of the wrist (measurement site) around which the cuff 20 is worn falls within the proper range based on the detection signals of the two gravity acceleration sensors 601 and 602. The detection signals are inputted from the A/D converter 61. That is, the position determining unit 102 determines whether the relative deviation width between the height of the wrist and the height of the virtual heart position is less than a predetermined value.

Figure 4:
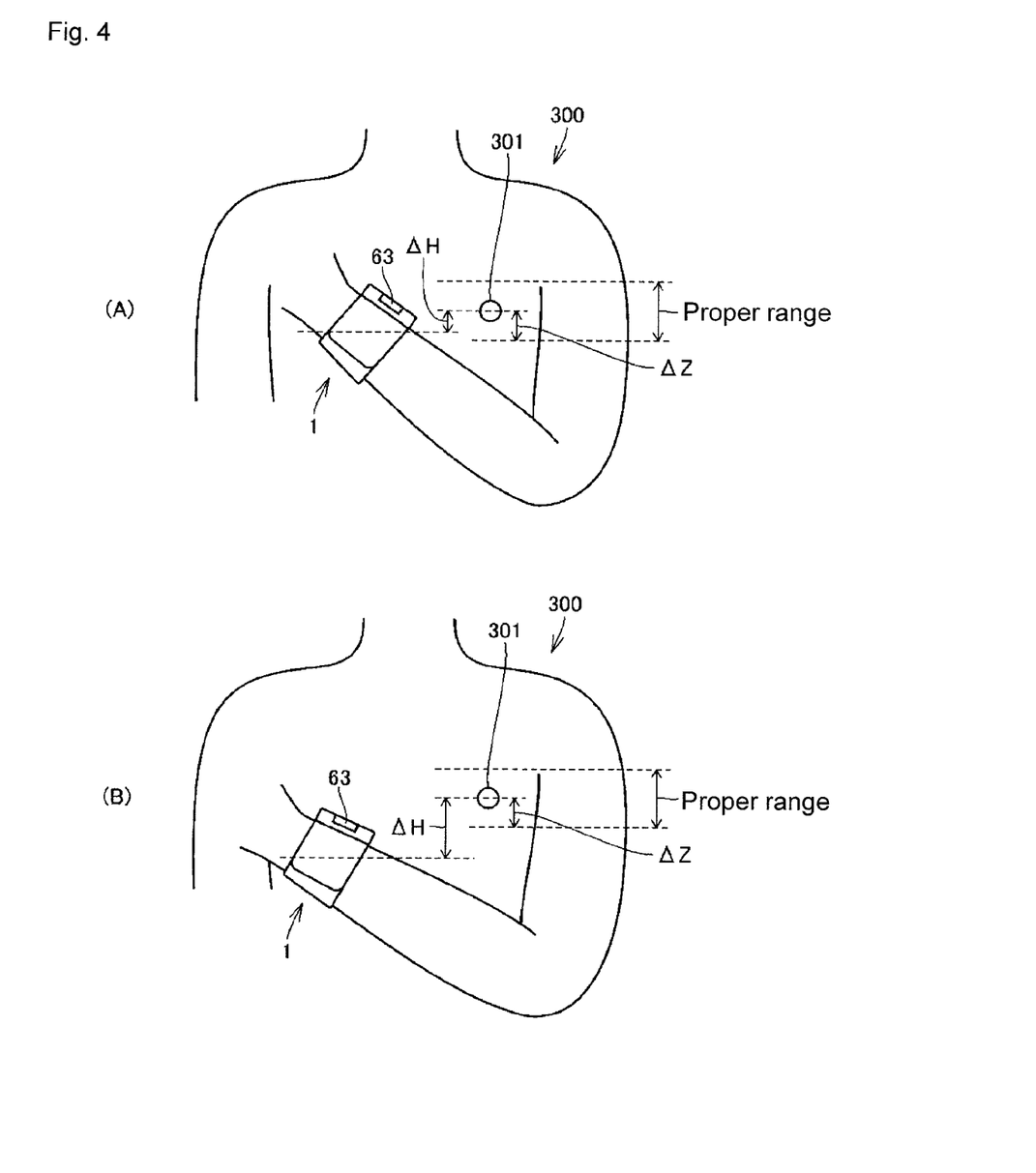
FIGS. 4(A) and 4(B) are views for describing a proper range of a position of a measurement site.

FIGS. 4(A) and 4(B) are views for describing a proper range of a position of a measurement site. FIG. 4(A) is a schematic diagram illustrating an example of a posture when the position of the measurement site falls within the proper range, and FIG. 4(B) is a schematic diagram illustrating an example of the posture when the position of the measurement site is out of the proper range.

Referring to FIGS. 4(A) and 4(B), the difference in height between a (virtual) heart position 301 of a person to be measured 300 and the predetermined reference position (the position of the measurement site) of the sphygmomanometer 1 is expressed by a "deviation width $\Delta H$". It is assumed that a proper range is less than a predetermined value $\pm \Delta Z$ based on the heart position 301. When the deviation width $\Delta H$ is less than the predetermined value $\Delta Z$, the position determining unit 102 determines that the position of the wrist falls within the proper range. On the other hand, when the deviation width $\Delta H$ is not less than the predetermined value $\Delta Z$, the position determining unit 102 determines that the position of the wrist is out of the proper range.

Similar to International Publication WO 2002/039893 (Patent Document 1) described above, the deviation width $\Delta H$ may be calculated as follows. First, the position determining unit 102 calculates the angle in the pitch direction and the angle in the roll direction of the wrist based on the two detection signals inputted from the A/D converter 61. Then, the position determining unit 102 calculates the difference in height (that is, the deviation width $\Delta H$) between the heart position and the reference position of the sphygmomanometer 1 by applying the calculated angles to a predetermined calculation formula. For example, the reference position of the sphygmomanometer 1 expresses a position near the center of the measurement site. However, the reference position is not limited thereto as long as the reference position is close to the position where the pressure is detected (the position where a target artery exists). The angle sensor 60 may be provided in the reference position.

According to one or more embodiments of the present invention, the deviation width $\Delta H$ is calculated by the technique described in Patent Document 1. However, the deviation width $\Delta H$ is not limited to such a technique, but may be calculated by another well-known technique.

According to one or more embodiments of the present invention, the two angles detected by the two gravity acceleration sensors 601 and 602 are once converted into the height (the difference in height), thereby determining whether the position of the wrist falls within the proper range. However, it is not always necessary to convert the two angles into the height. Alternatively, determination as to whether the position of the wrist falls within the proper range may be made based on whether the two angles fall within predetermined ranges.

The notification processing unit 104 notifies whether the position of the wrist (measurement site) falls within the proper range in order to guide a recommended measurement posture illustrated in FIG. 4(A). In the following description, the case in which the position of the wrist falls within the proper range is referred to as an "acceptable posture", and the case in which the position of the wrist is out of the proper range is referred to as an "unacceptable posture".

The notification processing unit 104 is connected to the light emitting unit 63. The notification processing unit 104 causes the light emitting unit 63 to emit blue light for the acceptable posture, and causes the light emitting unit 63 to emit red light for the unacceptable posture.

Figure 5:
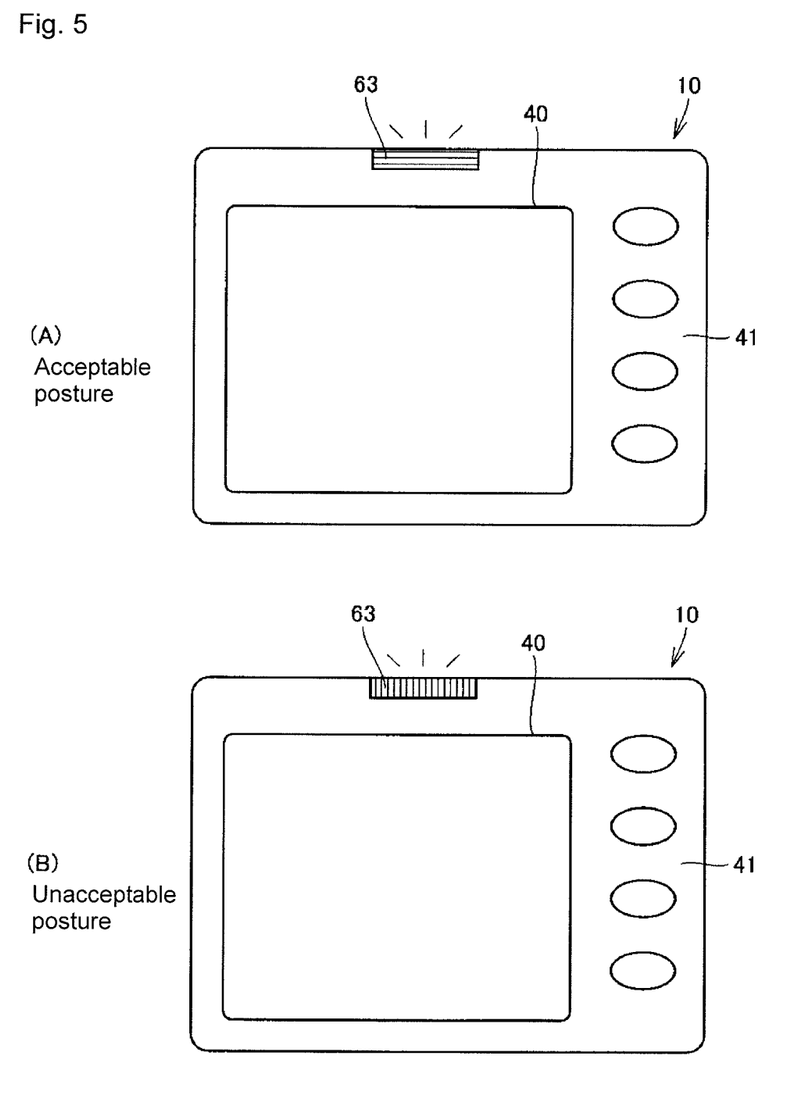
FIGS. 5(A) and 5(B) are views illustrating notification examples before the measurement starts.

FIGS. 5(A) and 5(B) are views illustrating notification examples before the start of measurement. FIG. 5(A) illustrates a notification example when the posture is acceptable, and FIG. 5(B) illustrates a notification example when the posture is unacceptable.

The light emitting unit 63 is disposed in a predetermined position of the surface (in which the display unit 40 is provided) of the main body 10. Because the color of the light emitting unit 63 is changed according to the position of the wrist, the person to be measured can intuitively recognize whether the measurement posture (the position of the wrist) is proper.

The notification processing unit 104 also notifies whether the position of the wrist falls within the proper range at the start of the measurement when the measurement result is displayed. That is, the light emitting unit 63 emits the blue light when the measurement result of the acceptable posture at the start of the measurement is displayed. The light emitting unit 63 emits the red light when the measurement result of the unacceptable posture at the start of the measurement is displayed. Therefore, the person to be measured or a physician is notified of the result whether the measurement is performed in the proper posture.

Not only the light emitting unit 63 but also the conventional buzzer 62 may notify whether the measurement posture is acceptable before the start of the measurement.

The emission color for the unacceptable posture is not limited to red, but may be orange or yellow. The user is intuitively easily aware of calling for attention by the colors. The emission color for the acceptable posture may be green or white in addition to blue. The user is intuitively easily aware of calling for attention by the colors.

Although the light emitting unit 63 emits two colors of light in the present embodiment, the light emitting unit 63 may emit only one color of light. In such cases, the light emitting unit 63 may be lit on for the acceptable posture while turned off for the unacceptable posture.

The time determining unit 106 is connected to the timing unit 45 that measures the current time and date, and determines whether the state of the acceptable posture continues for a predetermined time TA (for example, 2 seconds). The time determining unit 106 also determines whether the state of the unacceptable posture continues for a predetermined time TB (for example, 5 seconds). The time is counted with the time determining unit 106 by taking an instruction to start the measurement from the user as an opportunity. The time determining unit 106 initializes (resets) the count time when the determination result made by the position determining unit 102 is changed (unacceptable posture→acceptable posture or acceptable posture→unacceptable posture).

According to one or more embodiments of the present invention, the time TB used to determine the time of the unacceptable posture is longer than the time TA used to determine the time of the acceptable posture.

According to one or more embodiments of the present invention, the reference times (times TA and TB) for determining the time for which the state of the acceptable posture continues and the time for which the state of the unacceptable posture continues are previously fixed. However, the reference times are not limited thereto, but may be set and changed for each user.

According to one or more embodiments of the present invention, the time of the acceptable posture and the time of the unacceptable posture are counted based on the current date, time, and second obtained from the timing unit 45. However, the time of the acceptable posture and the time of the unacceptable posture may be counted by one timer. Alternatively, the time of the acceptable posture and the time of the unacceptable posture may be counted by two timers.

The measurement control unit 108 is connected to the pump drive circuit 53, the valve drive circuit 54, and the oscillation circuit 33 to control the measurement of the blood pressure of the person to be measured. The measurement control unit 108 calculates the blood pressure value (for example, a systolic blood pressure and a diastolic blood pressure) by a well-known technique (such as an oscillometric method). The measurement control unit 108 also calculates a pulse rate by a known technique.

Similar to the conventional technique, after the user inputs the instruction to start the measurement, the measurement control unit 108 starts the measurement by taking the fact that the time determining unit 106 determines that the time of the acceptable posture continues for the time TA or more as an opportunity. According to one or more embodiments of the present invention, the measurement control unit 108 also starts the measurement when the time determining unit 106 determines that the time of the unacceptable posture continues for the time TB or more.

The user issues the instruction to start the measurement irrespective of a button name (such as a measurement switch and a power switch) of the operation unit 41. That is, pressing the power switch is determined as the instruction to start the measurement when the operation of starting the measurement is performed by the power switch (not illustrated).

When the measurement is ended, the output control unit 110 displays the measurement values (that is, the systolic blood pressure, the diastolic blood pressure, and the pulse rate) as the measurement result on the display unit 40. Instead of or in addition to the display of the measurement result, the measurement result may be outputted to a printer (not illustrated) and the like.

The output control unit 110 also stores the measurement result and position identification data indicating whether the position of the measurement site falls within the proper range in the flash memory 43 while the measurement result and the position identification data are correlated with each other.

When the person to be measured is identified by the ID switch 41C, the measurement values and the position identification data are further stored while correlated with personal identification data identifying the person to be measured.

The output control unit 110 also has a function of displaying past measurement result (measurement data) stored in the flash memory 43. When the output control unit 110 displays the past measurement result, the notification processing unit 104 also notifies the user whether the currently-displayed measurement result is the proper posture using the color of the light emitting unit 63.

The operation of each functional block may be implemented by executing software stored in the memory unit 42, or at least one of the functional blocks may be implemented by hardware.

<Regarding Operation>
(Blood Pressure Measurement Process)

Figure 6:
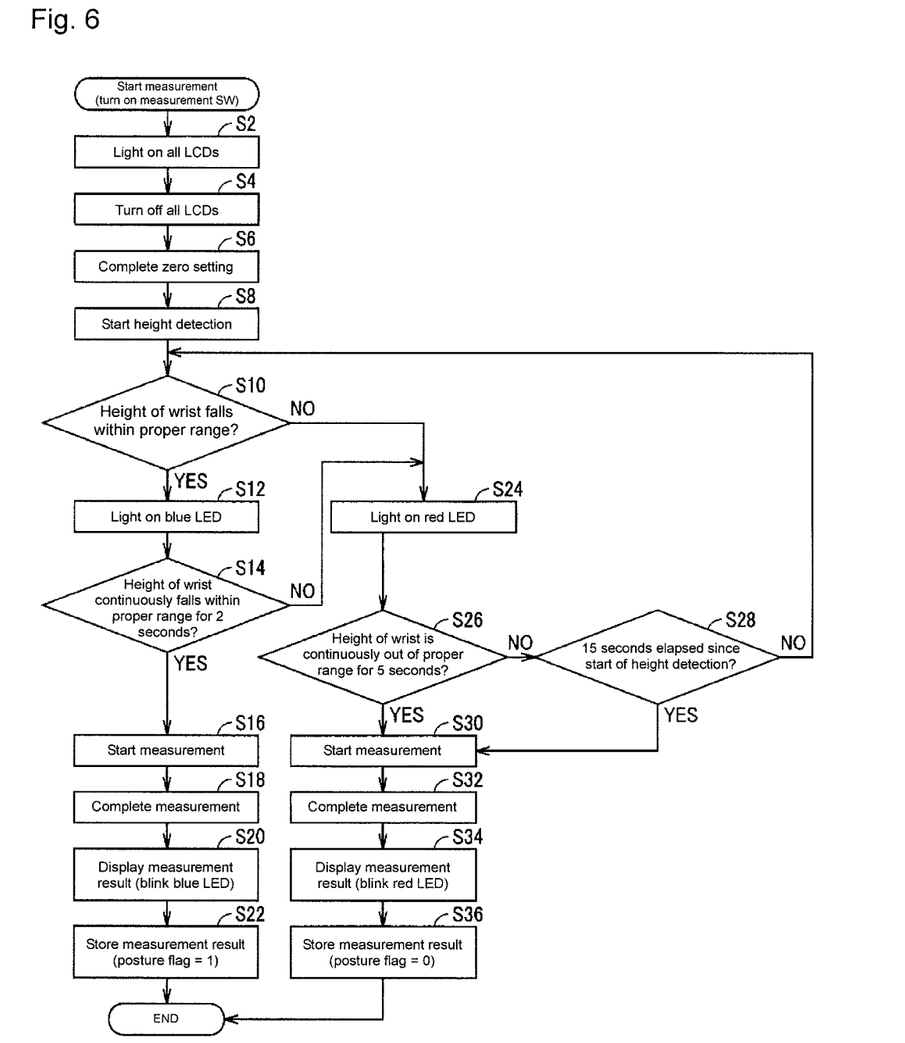
FIG. 6 is a flowchart illustrating a blood pressure measurement process performed by the sphygmomanometer according to an embodiment of the present invention.

FIG. 6 is a flowchart illustrating a blood pressure measurement process performed by the sphygmomanometer 1 according to an embodiment of the present invention. The process illustrated in the flowchart of FIG. 6 is previously stored as a program in the memory unit 42, and the CPU 100 reads and executes the program to implement the function of the blood pressure measurement process.

It is assumed that the person to be measured is previously identified by the ID switch 41C.

Referring to FIG. 6, when the measurement switch 41A is turned on, the power is applied to start the operation. First, all of the displays of the display unit 40 are lit on (step S2). Then all the displays of the display unit 40 are turned off (step S4), thereby enabling a display function to be confirmed.

Next, the CPU 100 completes zero setting, namely, initial reset (step S6). Specifically, a predetermined area of the memory unit 42 is initialized, the air of the air bladder 21 is exhausted, and the pressure sensor 32 is corrected to 0 mmHg. The time measured by the time determining unit 106 is reset. A value of a posture flag that acts as the above-described position identification data is set to "0" (out of the proper range).

The height detection of the wrist that is the measurement site is started when the zero setting is completed (step S8).

In order to detect the height of the wrist, the position determining unit 102 calculates the deviation width (difference in height) ΔH between the position of the measurement site (the reference position of the sphygmomanometer 1) and the virtual heart position based on the pieces of angular information on the front arm detected using the gravity acceleration sensor 601 in the pitch direction and the gravity acceleration sensor 602 in the roll direction.

The position determining unit 102 determines whether the height of the wrist falls within the proper range (step S10). That is, the determination whether the deviation width ΔH is less than the predetermined value ΔZ is made as illustrated in FIGS. 4(A) and 4(B).

When the height of the wrist falls within the proper range (YES in step S10), the position determining unit 102 sets the value of the posture flag to "1" (within the proper range), and the flow goes to step S12.

When the height of the wrist is out of the proper range (NO in step S10), the position determining unit 102 keeps the value of the posture flag at "0", and the flow goes to step S24.

In step S12, because the posture flag has the value of 1 (acceptable posture), the notification processing unit 104 causes the light emitting unit 63 to emit the blue light as illustrated in FIG. 5(A).

Next, because the posture flag has the value of 1, the time determining unit 106 determines that the position of the wrist is the acceptable posture and determines whether the height of the wrist continuously falls within the proper range for 2 seconds (step S14). It is assumed that the position determining unit 102 performs the position determining processing (the calculation of the deviation width ΔH) in the background in parallel to the determination processing performed in step S12.

The continuous time within the proper range is counted by taking the start of the position determination (step S8) performed by the position determining unit 102 as an opportunity immediately after the user issues the instruction to start the measurement. After the time of the unacceptable posture is measured (step S26 described below), the continuous time within the proper range is counted by taking the change from the unacceptable posture to the acceptable posture (the change of the flag value) as an opportunity.

According to one or more embodiments of the present invention, the position determination is made by pressing the measurement switch 41A. Therefore, according to one or more embodiments of the present invention, it is assumed that the time of the acceptable posture or unacceptable posture is counted by taking the start of the position determination as an opportunity. However, it is assumed that the time with the time determining unit 106 is inherently counted by taking the instruction to start the measurement from the user as an opportunity.

Not only the determination as to whether the position of the wrist falls within the proper range but also the determination as to whether the motion of the wrist is stopped may be made in step S14. The determination can be made based on whether an amount of change of the deviation width ΔH falls within a predetermined value.

When the height of the wrist continuously falls within the proper range for 2 seconds (YES in step S14), the measurement control unit 108 drives the pump 51 to start the measurement (step S16). The measurement control unit 108 measures (calculates) the systolic blood pressure, the diastolic blood pressure, and the pulse rate by a well-known technique.

When the height of the wrist does not continuously fall within the proper range for 2 seconds (NO in step S14), the position determining unit 102 changes the value of the posture flag from "1" to "0". Accordingly, the time determining unit 106 determines that the position of the wrist is changed from the acceptable posture to the unacceptable posture and resets the count time. Then the flow goes to step S24.

When the measurement performed by the measurement control unit 108 is completed after the determination that the position of the wrist is the acceptable posture is made (step S18), the output control unit 110 displays the measurement result on the display unit 40 (step S20). At this point, the notification processing unit 104 blinks the light emitting unit 63 in blue. In this manner, the user (typically, the person to be measured) is notified of the result that is measured in the proper measurement posture.

Then, the output control unit 110 stores the personal identification data of the person to be measured, the measurement results (the systolic blood pressure, the diastolic blood pressure, and the pulse rate), the measurement date and time, and the value (=1) of the posture flag in the flash memory 43 while the personal identification data of the person to be measured, the measurement results, the measurement date and time, and the value of the posture flag are correlated with one another (step S22). The operation is ended when the processing in step S22 ends.

In step S24, because the posture flag has the value of 0 (unacceptable posture), the notification processing unit 104 lights on the light emitting unit 63 in red as illustrated in FIG. 5(B).

Because the posture flag has the value of 0, the time determining unit 106 determines that position of the wrist is the unacceptable posture and determines whether the height of the wrist is continuously out of the proper range for 5 seconds (step S26). In this case as well, it is assumed that the position determining unit 102 performs the position determining processing (the calculation of the deviation width ΔH) in the background in parallel to the determination processing performed in step S26.

Counting the continuous time that is out of the proper range may be similar to the processing in step S14. After the time of the acceptable posture is measured (step S14), the continuous time that is out of the proper range is counted by taking the change from the acceptable posture to the unacceptable posture (the change of the flag value) as an opportunity.

Not only the determination as to whether the position of the wrist is out of the proper range but also the determination as to whether the motion of the wrist is stopped out of the proper range may be made similar to the processing in step S14. Therefore, the presence or absence of a measurement intention of the person to be measured can sufficiently be determined.

When determined that the height of the wrist is continuously out of the proper range for 5 seconds (YES in step S26), the flow goes to step S30.

When determined that the height of the wrist is not continuously maintained for 5 seconds in step S26 (NO in step S26), the flow goes to step S28.

In step S28, the time determining unit 106 determines whether, for example, 15 seconds has elapsed since the height detection is started (that is, since the instruction to start the measurement is issued). After the height detection is started, the elapsed time is counted independently of the time count in steps S14 and S26. Such elapsed time may be calculated by the output from the timing unit 45, or a timer may separately be provided.

When 15 seconds has elapsed (YES in step S28), both the states of the acceptable posture and unacceptable posture are not maintained for the predetermined periods of time (2 seconds and 5 seconds). In this case as well, assuming that the position of the wrist is the unacceptable posture, the flow goes to step S30. In this manner, the measurement is prevented from not being started for a long time.

When 15 seconds has not elapsed (NO in step S28), the position determining unit 102 changes the value of the posture flag from "0" to "1". Accordingly, the time determining unit 106 determines that the position of the wrist is changed from the unacceptable posture to the acceptable posture and resets the count time. Then, the flow returns to step S10.

In step S30, similar to the processing in step S16, the measurement control unit 108 drives the pump 51 to start the measurement. The measurement control unit 108 measures (calculates) the systolic blood pressure, the diastolic blood pressure, and the pulse rate by a well-known technique.

When the measurement performed by the measurement control unit 108 is completed after the determination that the position of the wrist is the unacceptable posture is made (step S32), the output control unit 110 displays the measurement result on the display unit 40 (step S34). At this point, the notification processing unit 104 blinks the light emitting unit 63 in red. Therefore, the user (typically, the person to be measured) is notified of the result that is measured in the unrecommended measurement posture by lighting on the red LED.

Then, the output control unit 110 stores the personal identification data of the person to be measured, the measurement results (the systolic blood pressure, the diastolic blood pressure, and the pulse rate), the measurement date and time, and the value (=0) of the posture flag in the flash memory 43 while the personal identification data of the person to be measured, the measurement results, the measurement date and time, and the value of the posture flag are correlated with one another (step S36). The operation is ended when the processing in step S36 ends.

As described above, similar to the conventional sphygmomanometer, the sphygmomanometer 1 has the function of notifying the user of the proper or improper posture. This is because the measurement is desirably performed in the proper measurement posture (the position of the wrist falls within the proper range) in order to obtain the accurate measurement result.

Similar to the conventional technique, the measurement is automatically started when the state of the acceptable posture illustrated in FIG. 4(A) is continuously detected for 2 seconds. Therefore, the high-reliability measurement result can be obtained by the proper measurement posture similar to the conventional technique.

Additionally, according to one or more embodiments of the present invention, the time determining unit 106 resets the count time when the determination result made by the position determining unit 102 is changed. Even if the position of the wrist is out of the proper range, the measurement is started when the wrist continuously exists in the position for 5 seconds. Even in the unrecommended position (position out of the proper range) illustrated in FIG. 4(B), when the position of the wrist is continuously maintained in the position for 5 seconds, there is a high probability that the person to be measured is waiting for the start of the measurement. According to one or more embodiments of the present invention, usability is improved by starting the measurement even in such cases.

That is, the inconvenience of the user who cannot move the wrist into the proper range can be reduced. Moreover, for the user who does not know the correct measurement posture because the user does not read an instruction manual or the like, an uncomfortable feeling caused by the measurement not being started for a long time can be reduced.

The sphygmomanometer 1 according to one or more embodiments of the present invention can be used by a plurality of users. Even if a single sphygmomanometer 1 is used by a person who knows the proper measurement posture, a person who does not know the proper measurement posture, and a person who cannot take a proper measurement position or the like, the measurement can be started in a state suitable to each user.

According to one or more embodiments of the present invention, in displaying the measurement result, the user is further notified whether the position of the measurement site falls within the proper range while correlated with the measurement result. Accordingly, the user or the physician can know whether the currently-displayed measurement result is a highly reliable value. Therefore, the physician can make use of the measurement result in a later diagnosis.

Even if the user does not read the instruction manual, the user can be aware of the wrong measurement posture, and can recognize the correct posture. That is, such notification leads to the awareness of the correct measurement posture by reviewing the instruction manual and the like. As a result, even if the user does not know the proper measurement posture, the user can perform the measurement in the proper measurement posture (at the same height as the heart) from then on.

According to one or more embodiments of the present invention, the user is notified whether the position of the measurement site falls within the proper range by the contrastive two colors of the blue and red. Before the measurement is started, the user can recognize that the color is changed (red→blue) by the motion of the wrist. Accordingly, compared with the notification by the conventional buzzer, the proper posture can more sensuously be recognized by the user.

(Display Example)

Figure 7:
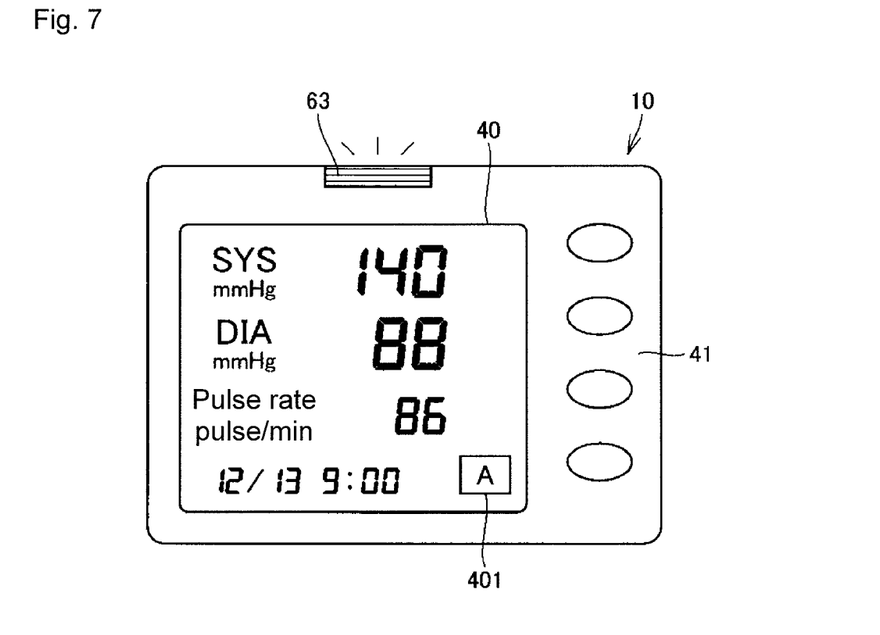
FIG. 7 is a view illustrating a display example of measurement result in an embodiment of the present invention.

FIG. 7 is a view illustrating a display example of measurement result in according to an embodiment of the present invention.

Referring to FIG. 7, when the blood pressure is measured, the output control unit 110 displays the systolic blood pressure (SYS), the diastolic blood pressure (DIA), the pulse rate, and the measurement date and time on the display unit 40 (steps S20 and S34). Additionally, information 401 specifying the person to be measured may be displayed on the display unit 40 based on the personal identification data.

According to one or more embodiments of the present invention, the light emitting unit 63 emits the blue or red light in displaying the measurement result. Therefore, the user and the like can know whether the currently-displayed measurement result has high reliability.

(Data Structure Example)

Figure 8:
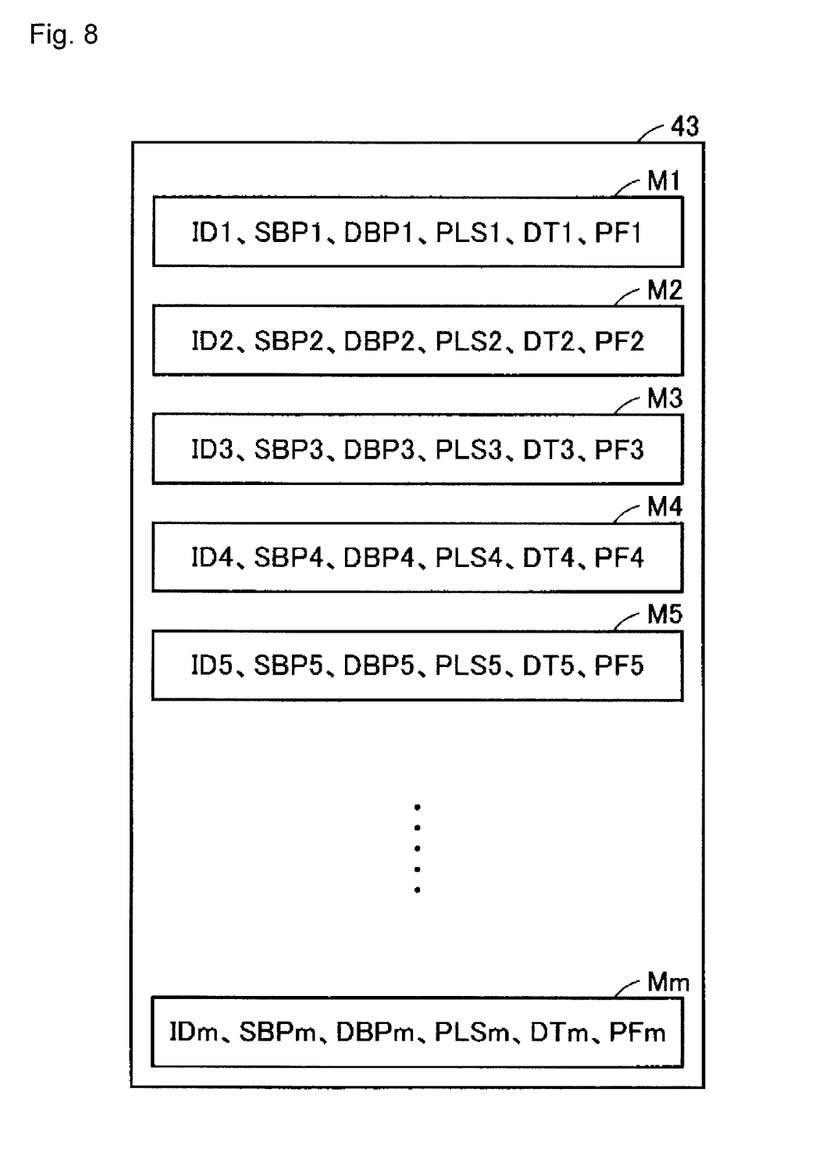
FIG. 8 is a view illustrating a data structure example of measurement result information in an embodiment of the present invention.

FIG. 8 is a view illustrating a data structure example of measurement result information in an embodiment of the present invention.

Referring to FIG. 8, a plurality of pieces of measurement data M1 to Mm (m =1, 2, 3, . . . ) in a record format are stored as measurement result information in the flash memory 43.

Each piece of measurement data includes personal identification data ID (=A, B, . . . ), systolic blood pressure data SBP indicating the systolic blood pressure, diastolic blood pressure data DBP indicating the diastolic blood pressure, pulse rate data PLS indicating the pulse rate, measurement date and time data DT, and the posture flag PF (=1, 0).

Each piece of data is not limited to the storage format in which the record is used, but it is only necessary to store the pieces of data while the pieces of data are correlated with each other in each measurement.

(Measurement Recording and Displaying Process)

As described above, because the posture flag is stored in each measurement while correlated with the measurement value, whether the position of the wrist falls within the proper range can be displayed in displaying the measurement record (the past measurement value).

Figure 9:
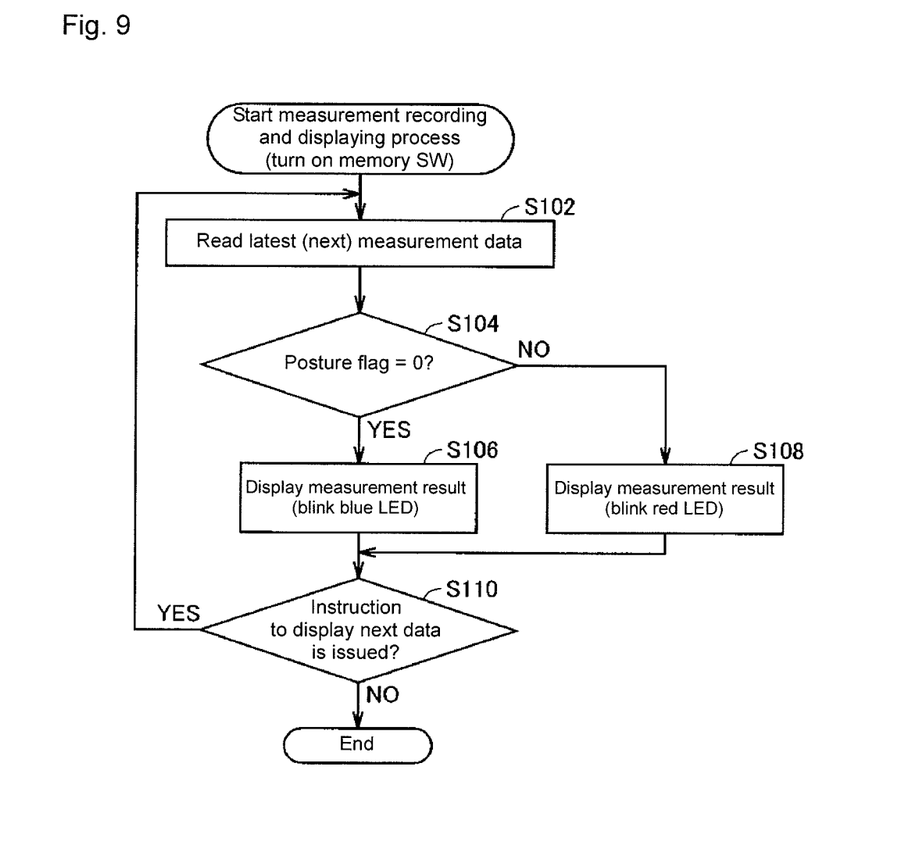
FIG. 9 is a flowchart illustrating a measurement recording and displaying process in an embodiment of the present invention.

FIG. 9 is a flowchart illustrating a measurement recording and displaying process in an embodiment of the present invention. The process illustrated in the flowchart of FIG. 9 is also previously stored as the program in the memory unit 42, and the CPU 100 reads and executes the program to implement the function of the measurement recording and displaying process.

At this point, it is also assumed that the person to be measured is previously specified by the ID switch 41C.

Referring to FIG. 9, when the memory switch 41D is turned ON, the power is turned on to start the operation. First, the output control unit 110 reads the latest measurement data of the specified person to be measured (step S102). Specifically, the measurement data correlated with the personal identification data of the specified person to be measured is searched in the plurality of pieces of measurement data stored in the flash memory 43. The latest measurement data is read from the pieces of measurement data correlated with the personal identification data of the specified person to be measured.

Determination is made as to whether the posture flag included in the read measurement data has the value of 0 (step S104). When the posture flag has the value of 0 (YES in step S104), the measurement result is displayed while the light emitting unit 63 emits blue light (step S106). When the posture flag does not have the value of 0 (NO in step S104), the measurement result is displayed while the light emitting unit 63 emits red light (step S108).

The display similar to the example of FIG. 7 and the lighting of the light emitting unit 63 may also be performed in steps S106 and S108.

The output control unit 110 determines whether an instruction to display the next data is issued (step S110). When the instruction to display the next data is issued (YES in step S110), the flow returns to step S102 to repeat the pieces of processing. From the second time, it is assumed that the latest measurement data next to the displayed measurement data is read in step S102.

On the other hand, when the instruction to display the next data is not issued (NO in step S110), the operation is ended.

Thus, even in displaying the past measurement result, the user is notified every time whether the measurement posture is proper by the color of the light emitting unit 63. Accordingly, even if the user does not know the proper measurement posture after the measurement is performed several times, as the user sees the plurality of measurement results, the user may be aware of the difference in color to obtain an opportunity to learn the proper posture.

<Modification>

According to one or more embodiments of the present invention, the light emitting unit 63 is lit on and/or blinked only in detecting the height before the measurement and displaying the measurement result. Alternatively, the height of the wrist is detected during the measurement, and the user may be notified of the measurement result by the color of the light emitting unit 63.

According to one or more embodiments of the present invention, the light emitting unit 63 notifies the user whether the position of the wrist falls within the proper range, but embodiments of the present invention are not limited thereto. For example, the "acceptable posture" and the "unacceptable posture" may be displayed in a predetermined area of the display unit 40. Therefore, the user can be notified more reliably whether the measurement posture is proper. Such notification is effective to the user who does not recognize the proper measurement posture because the user does not read the instruction manual.

According to one or more embodiments of the present invention, the light emitting unit 63 is provided only for notifying the user of the proper or improper posture, but embodiments of the present invention are not limited thereto. For example, the whole or part of the display unit 40 may be lit on in blue or red.

Instead of or in addition to the notification by the light emitting unit 63, the user may be notified of the proper or improper posture by the buzzer 62. In such cases, the proper and improper postures may be distinguished by the high and low or strong and weak sounds of the buzzer 62.

The user may be notified of the proper or improper posture by a difference in vibration. In such cases, the sphygmomanometer 1 includes a vibration output unit (not illustrated) that outputs the vibration and a vibration drive circuit (not illustrated) that drives the vibration output unit, and the vibration drive circuit may be connected to the notification processing unit 104 of the CPU 100.

The sphygmomanometer 1 according to one or more embodiments of the present invention has the functions of detecting the proper or improper measurement posture and notifying the user of the proper or improper measurement posture, and the sphygmomanometer 1 has the specification in which the measurement can be performed even for the unacceptable posture. However, the sphygmomanometer 1 may have a mode in which the measurement can be performed only for the acceptable posture like the conventional technique and a mode as described above in which the measurement can be performed for the unacceptable posture.

In such cases, because the mode can be selected according to the convenience of the user of the sphygmomanometer 1, the usability can further be improved.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS 1 electronic sphygmomanometer
10 main body
20 cuff 21 air bladder
30 air system
31 air tube
32 pressure sensor
33 oscillation circuit
40 display unit
41 operation unit
41A measurement switch
41B setting switch
41C ID switch
41D memory switch
42 memory unit
43 flash memory
44 power supply
45 timing unit
46 data input/output unit
50 adjustment mechanism
51 pump
52 valve
53 pump drive circuit
54 valve drive circuit
60 angle sensor
61 A/D converter
62 buzzer
63 light emitting unit
100 CPU
102 position determining unit
104 notification processing unit
106 time determining unit
108 measurement control unit
110 output control unit
132 recording medium
300 person to be measured
301 heart position
601, 602 gravity acceleration sensor

The invention claimed is:

1. An electronic sphygmomanometer comprising:
a cuff (20) that is worn around a predetermined measurement site;
a pressure sensor (32) that detects a cuff pressure signal indicating a pressure in the cuff;
an angle sensor (60) that detects an angle of the cuff with respect to a predetermined reference direction;
a position determining unit (102) that determines whether a height of the measurement site falls within a proper range based on an output from the angle sensor;
a notification unit (62, 63) that notifies whether the height of the measurement site falls within the proper range;
a time determining unit (106) that determines whether a first time indicating a time in which the height of the measurement site continuously falls within the proper range is not less than a first reference time; and
a measurement control unit (106) that controls measurement of a blood pressure based on the cuff pressure signal by taking the determination that the first time is not less than the first reference time as a first opportunity, wherein
the time determining unit determines whether a second time indicating a time in which the height of the measurement site is continuously out of the proper range is not less than a second reference time longer than the first reference time,
the measurement control unit starts the measurement by taking the determination that the second time is not less than the second reference time as a second opportunity, and
wherein the measurement control unit completes measurement after said determination unit determines said first time or said second time has been satisfied to create said first opportunity or said second opportunity, and
the notification unit notifies whether the height of the measurement site falls within the proper range while the height of the measurement site is correlated with a measurement result when the measurement control unit outputs the measurement result.

2. The electronic sphygmomanometer according to claim 1, wherein the time determining unit initializes a currently-measured time when a determination result of the position determining unit is changed.

3. The electronic sphygmomanometer according to claim 1, further comprising a storage unit (43) in which height identification data indicating whether the height of the measurement site falls within the proper range is stored while correlated with the measurement result.

4. The electronic sphygmomanometer according to claim 3, wherein the measurement result and the height identification data are stored in the storage unit while correlated with personal identification data identifying a person to be measured.

5. The electronic sphygmomanometer according to claim 1, wherein the time determining unit further determines whether an elapsed time since a user issues an instruction to start the measurement is not less than a third time which is longer than the second reference time, and the measurement control unit starts the measurement by taking the determination that the elapsed time is not less than the third reference time as a third opportunity and wherein the measurement control unit completes measurement after said determination unit determines said first opportunity and said second opportunity have not been satisfied and said third time has been satisfied to create said third opportunity for said measurement.

6. The electronic sphygmomanometer according to claim 1, wherein the notification unit includes a light emitting unit (63) that emits first color light and second color light, and a notification processing unit (104) that, in order to notify whether the height of the measurement site falls within the proper range, causes the light emitting unit to emit the first color light when the height of the measurement site falls within the proper range, and causes the light emitting unit to emit the second color light when the height of the measurement site is out of the proper range.

7. The electronic sphygmomanometer according to claim 1, wherein the notification unit includes a display unit (40) that displays the measurement result, and a notification processing unit (104) that displays information indicating whether the height of the measurement site falls within the proper range on the display unit in order to notify whether the height of the measurement site falls within the proper range.

* * * * *